United States Patent [19]

Motion et al.

[11] Patent Number: 5,656,668
[45] Date of Patent: Aug. 12, 1997

[54] HYDROXY ALKYL AMIDES OF DICARBOXYLIC ACIDS AND THEIR USE IN COSMETIC COMPOSITIONS

[75] Inventors: Keith Robert Motion, Hythe; Angela Janousek, Canterbury; Stephen David Watkins, Nr Ashford, all of United Kingdom

[73] Assignee: Quest International B.V., Naarden, Netherlands

[21] Appl. No.: 416,719

[22] PCT Filed: Oct. 4, 1993

[86] PCT No.: PCT/GB93/02061

§ 371 Date: May 30, 1995

§ 102(e) Date: May 30, 1995

[87] PCT Pub. No.: WO94/07844

PCT Pub. Date: Apr. 14, 1994

[30] Foreign Application Priority Data

Oct. 7, 1992 [EP] European Pat. Off. ............. 92309140
Sep. 27, 1993 [EP] European Pat. Off. ............. 93307620

[51] Int. Cl.⁶ .................... A61K 31/195; C07C 229/24
[52] U.S. Cl. .................... 514/564; 514/558; 514/561; 514/563; 514/616; 514/844; 514/845; 514/880; 514/881; 554/35; 554/36; 554/106; 564/152; 564/155; 564/159; 564/201
[58] Field of Search ..................... 514/558, 561, 514/563, 564, 616, 844, 845, 880, 881; 564/152, 155, 159, 201; 554/106, 35, 36

[56] References Cited

U.S. PATENT DOCUMENTS 4,978,786  12/1990  Messina et al. ................ 564/160

FOREIGN PATENT DOCUMENTS 420722  4/1991  European Pat. Off. .
450527  10/1991  European Pat. Off. .
482860  4/1992  European Pat. Off. .
2604554  8/1977  Germany .

OTHER PUBLICATIONS

Linfield, et al, JAOCS, vol. 65, No. 5 (May 1988) pp. 820–825.
Michich, T.J. et al: "Wetting properties of nonionics from branched fatty diamides", JAOCS, J.A., Oil Chem Soc., 65(5), 820–5 1988.

Primary Examiner—Shailendra Kumar
Attorney, Agent, or Firm—Cushman Darby & Cushman IP Group of Pillsbury Madison & Sutro, LLP

[57] ABSTRACT

A class of pseudoceramide having the formula shown in which: R1 is a hydrocarbon group; R2–R8 are each independently H or $CH_3$; R9 and R10 are each independently H or hydrocarbon group of up to 24 C atoms; X1 and X2, are independently H or OH; Y1 and Y2 are H or OH, at least one of Y1 and Y2 being OH; wherein the C atom Z, with associated R9 and R10, can be absent; and the C atoms W, with associated R7 and Y2, can be absent, is disclosed. These find use in compositions, particularly cosmetic compositions, suitable for topical application to skin, hair or nails.

12 Claims, 3 Drawing Sheets

Pseudoceramide I

Compound 10

10 : R = n-C₁₆H₃₃

HYDROXY ALKYL AMIDES OF DICARBOXYLIC ACIDS AND THEIR USE IN COSMETIC COMPOSITIONS

This is a 371 of PCT/GB93/02061; filed Oct. 4, 1993.

FIELD OF THE INVENTION

This invention concerns cosmetic compositions, particularly those including so-called "pseudoceramides", and relates to a novel class of pseudoceramides and their use in the treatment of skin, hair and nails.

BACKGROUND OF THE INVENTION

Ceramides are a group of naturally occurring compounds having the formula shown in FIG. 1, where m=10–16 and n=12–24. Ceramides and ceramide derivatives are believed to play an important role in the water permeability properties of the skin, functioning to give increased strength to the skin structure to decrease water loss and so improve the condition of the skin, and it is known to use ceramides and ceramide derivatives as components of skin care compositions.

Certain non-naturally occurring variants of ceramides, known as pseudoceramides, have been synthesised or proposed. Generally these are designed to have certain properties similar to those of ceramides and to mimic the behaviour of ceramides in relation to the skin so as to be usable in skin care compositions as cheaper substitutes in place of naturally occurring skin ceramides.

Known pseudoceramides include those described in EP 0420722 A of L'Oreal and EP 0482860 A of Unilever.

The present invention is based on a novel class of pseudoceramides.

SUMMARY OF THE INVENTION

In one aspect the present invention provides compounds of the formula shown in FIG. 2, in which:

R1 is a hydrocarbon group;

R2–R8 are each independently H or $CH_3$;

R9 and R10 are each independently H or a hydrocarbon group of up to 24 carbons;

X1 and X2 are independently H or OH;

Y1 and Y2 are H or OH, at least one of Y1 and Y2 being OH;

wherein the C atom Z, with associated R9 and R10, can be absent; and the C atoms W, with associated R7 and Y2, can be absent.

R1 may be an aliphatic hydrocarbon, and preferably has 10–24 C atoms, more preferably 16–18 C atoms.

Compounds in accordance with the invention have certain properties similar to those of naturally occurring skin ceramides, and can thus be considered to constitute a novel class of pseudoceramides.

The compounds of the invention thus find application in the treatment of skin, hair and nails.

In a further aspect the invention thus provides a composition, particularly a cosmetic composition, suitable for topical application to skin, hair or nails, comprising a compound in accordance with the invention.

The invention also covers use of a compound in accordance with the invention as an agent for skin water barrier repair, for improving nails and/or for improving hair.

The composition may include one or more compounds in accordance with the invention, conveniently in an amount in the range 0.00001 to 50% by weight, preferably 0.001 to 20% by weight, more preferably 0.1 to 10% by weight, eg 0.8 to 5.0% by weight.

The composition preferably includes a suitable carrier vehicle for the compound. This will generally be a cosmetically acceptable vehicle which acts as a diluent, dispersant or carrier to enable the compound to be dispersed onto the skin, hair or nails and distributed thereon.

Suitable carrier vehicles include water, liquid or solid emollients, solvents, humectants and powders. Examples of these types of vehicles, which can be used singly or as mixtures, are given in EP 0482860 A.

The carrier vehicle will usually form from 10 to 99.9% by weight, preferably from 50 to 90% by weight, of the composition, and can, in the absence of other cosmetic adjuncts, form the balance of the composition.

Optional skin benefit materials and cosmetic adjuncts may also be included.

Compounds in accordance with the invention are found to have excellent emulsifying, gelling and thickening properties and are well suited to use in formulations in the form of viscous emulsions or gels.

A particularly convenient form of the composition according to the invention is an emulsion, in which case an oil or oily material will normally be present, together with an emulsifier (if required) to provide either a water-in-oil emulsion or an oil-in-water emulsion, depending largely on the average hydrophilic-lyophilic balance (HLB) of the emulsifier employed.

The composition according to the invention can optionally comprise one or more oils or other materials having the properties of an oil.

Examples of suitable oils include mineral oil and vegetable oils, and oil materials, such as those already proposed as emollients in EP 0482860 A. Other oils or oily materials include silicone oils, both volatile and non-volatile, such as polydimethyl siloxanes.

The oil or oily material, when present for the purposes of forming an emulsion, will normally form up to 90% by volume, preferably from 10 to 80% by volume, of the composition.

The composition according to the invention can also optionally comprise one or more emulsifiers the choice of which will normally determine whether a water-in-oil or an oil-in-water emulsion is formed.

When a water-in-oil emulsion is required, the chosen emulsifier or emulsifiers should normally have an average HLB value of from 1 to 8. When an oil-in-water emulsion is required, a chosen emulsifier or emulsifiers should have an average HLB value greater than 8.

Examples of suitable emulsifiers are given in EP0482860 A.

It is to be understood that two or more emulsifiers can be employed if desired.

The amount of emulsifier-or mixtures thereof to be incorporated in the composition of the invention when appropriate is typically from 1 to 50% by weight, preferably from 2 to 20% by weight, and more preferably from 2 to 10% by weight of the composition.

The composition of the invention can also comprise water, usually up to 98% by volume, preferably from 5 to 80% by volume.

The composition of the invention can also optionally comprise a high molecular weight silicone surfactant which can also act as an emulsifier, in place of or in addition to the optional emulsifier(s) already referred to. The silicone surfactant is typically a high molecular weight polymer of dimethyl polysiloxane with polyoxyethylene and/or polyoxypropylene side chains as disclosed in EP 0482860 A.

The composition may take a variety of forms, eg skin and nail creams and lotions, sun-tan products, soaps, bath oils, lotions and foams, shampoos, hair conditioners etc.

The composition of the invention can, for example, be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer.

For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a composition in accordance with the invention.

In a further aspect, the present invention also provides a method of treating skin, hair or nails, comprising topical application of a composition in accordance with the invention.

Considering now the compounds of the invention, R1 is preferably aliphatic and preferably has 10–24 C atoms, more preferably 10–18 C atoms.

Examples of compounds within the scope of the general formula that have been synthesised are shown in FIGS. 3 to 9.

The compound of FIG. 3 is referred to herein as pseudoceramide I, and in this compound:

$R1=C_{16}H_{33}$
$R2-R6, R8-R10=H$
$X1, X2=OH$
$Y1=OH$
W, Y2 and R7 are absent.

The compounds of FIG. 4 include 3 compounds referred to herein as pseudoceramide E, G and H respectively. In these compounds:

$$R1 = \begin{array}{ll} C_{16}H_{33} & (E) \\ C_{12}H_{25} & (G) \\ C_{14}H_{29} & (H) \\ C_{10}H_{21} & \\ C_{8}H_{17} & \end{array}$$

$R2-R6, R8=R10=H$
$X1, X2=H$
$Y1=OH$
W, Y2 and R7 are absent.

In the compound of FIG. 5;
$R1=C_{14}H_{29}$
$R2-R10=H$
$X1, X2=H$
$Y1, Y2=OH$

In the compound of FIG. 6;
$R1=C_{14}H_{29}$
R2–R6 and R8=H
$X1, X2=H$
$Y1=OH$
W, Y2 and R7 are absent
Z, R9 and R10 are absent.

In the compound of FIG. 7:
$R1=C_{12}H_{25}$
$R2-R10=H$
$X1, X2=H$
$Y1=H$
$Y2=OH$ In the compound of FIG. 8:
$R1=C_{14}H_{29}$
$R2-R10=H$
$X1, X2=H$
$Y1=OH$
$Y2=H$ The compound of FIG. 9 is referred to herein as compound 10, and in this compound:

$R1=C_{14}H29$
R2–R6 and R8=H
$X1, X2=H$
$Y1=OH$
W, Y2 and R7 are absent
$R9=C_{16}H_{33}$
R10 is absent.

The currently preferred compounds for skin treatment purposes are pseudoceramide E and pseudoceramide H.

The compounds are conveniently prepared by treatment of the corresponding alkylaminoalcohol/diol/triol produce a diamide, eg by use of the diester method of the acid choride method. These are standard methods of amide preparation well known to those skilled in the art. The relevant alkylaminoalcohol/diol/triol can be prepared using known techniques, eg as described in Bull. Chim. Soc. Fr. (1943), 10, 347.

In another aspect, the invention thus provides a method of preparing a compound in accordance with the invention, comprising treating an alkylaminoalcohol/diol/triol to produce the corresponding diamide.

The invention will be further explained, by way of illustration, in the following examples.

EXAMPLE 1

Figure 1:
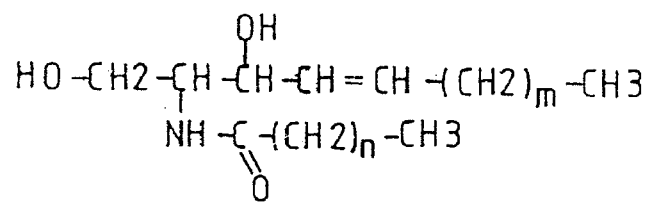
FIG. 1 shows the formula of ceramide.
Figure 2:
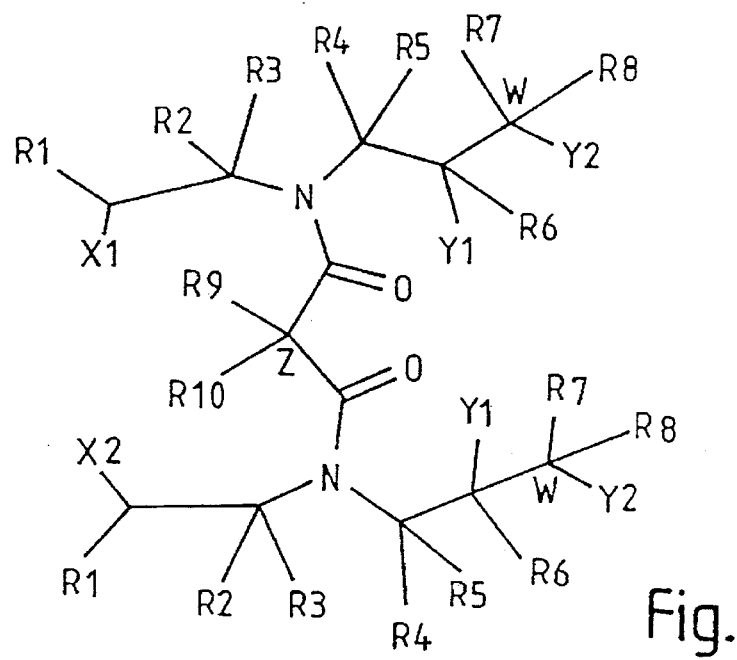
FIG. 2 shows the general formula of compounds in accordance with the invention.
Figure 3:
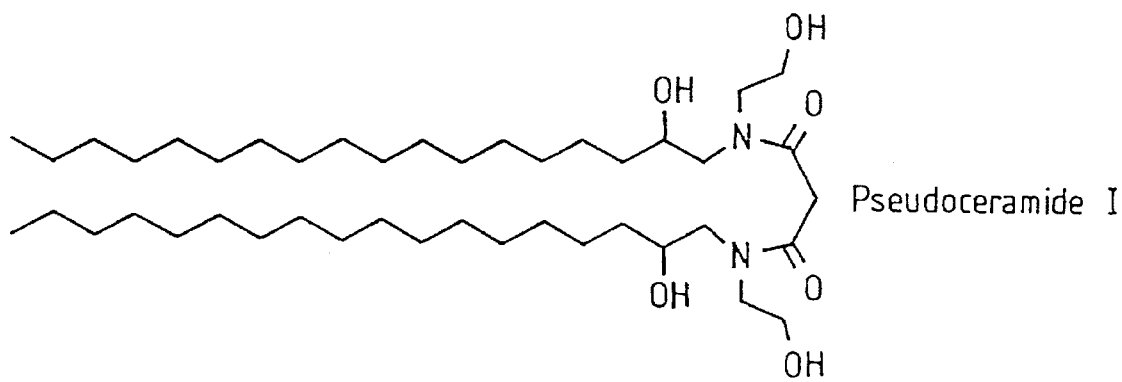
FIGS. 3 to 9 show the formulae of particular compounds in accordance with the invention.
Figure 4:
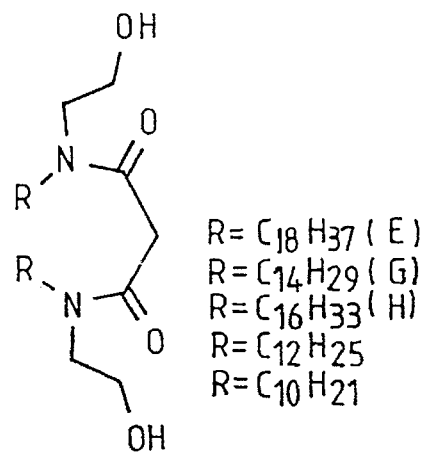
Figure 5:
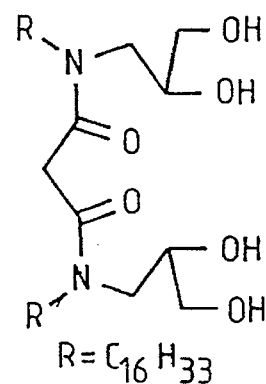
Figure 6:
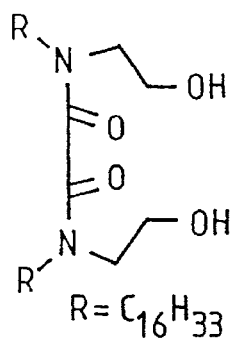
Figure 7:
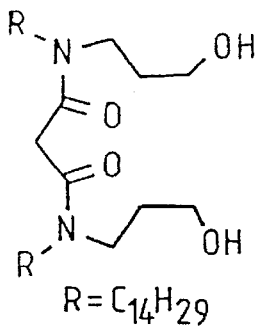
Figure 8:
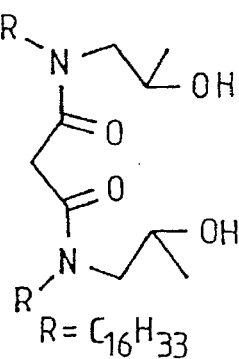

Pseudoceramide H (also known by the Trade Name Questamide H), the formula of which is shown in FIG. 4, was prepared as follows:

N-hexadecyl-2-aminoethanol was prepared by the method described in Bull. Chim. Soc. Fr. (1943), 10, 347.

The corresponding diamide was produced by the diester method, as follows.

N-Hexadecyl-2-aminoethanol (0.06 mol) and cylclohexane (300 ml) were charged to a 500 ml reaction flask fitted with dropping funnel, overhead stirrer and Dean-Stark apparatus with condenser. The mixture was heated with stirring to reflux, and dimethyl malonate (0.03 mol) was added over 10 minutes. The stirring/heating was continued until no more methanol appeared. The reaction mixture was cooled and filtered to give the diamide (13.2 g, 69% yield).

In combination with other intercellular lipids such as cholesterol and fatty acids, Pseudoceramide H forms "structured" liquid crystals similar to those formed by natural ceramide. Pseudoceramide H also forms a gel-like structure with squalene in a similar way to natural ceramide.

EXAMPLE 2

Figure 9:
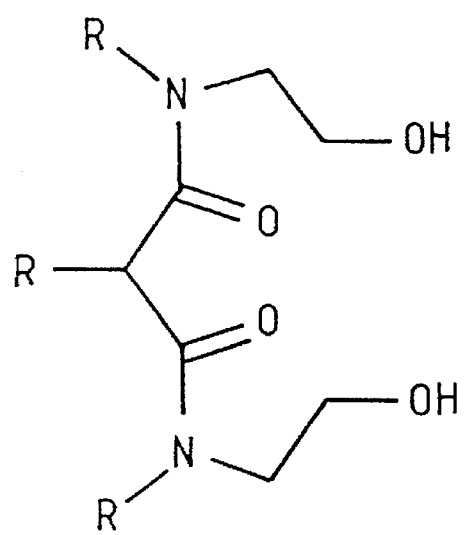

Compound 10, The formula of which is shown in FIG. 9, was prepared as follows:

N-2-hydroxyethylcetylamine (20 g, 0.070 mol), dimethyl hexadecylmalonate (13.5 g, 0.035 mol) and cyclohexane (100 ml) were charged to a 250 ml reaction flask equipped with a Dean-Stark take off. The mixture was stirred with heating to reflux for 190 hrs. The solvent was removed in vacuo, leaving an off-white solid residue. This was recrystallised from dichloromethane, and dried to give compound 10, m.pt. 50°–51° C. IR and NMR spectra support the structure as shown in FIG. 9.

EXAMPLE 3

A cosmetic skin cream composition, particularly suited to use on dry skin, was made from the following ingredients:

| CTFA NAME | INGREDIENTS | wt % |
|---|---|---|
| Phase A | | |
| Carbomer | Carbopol 940 | 0.34 |
| Propylene glycol | | 3.45 |
| Methyldibromo glutaronitrile and phenoxyethanol | Euxyl K400 | 0.10 |
| Triethanolamine | | 1.62 |
| Deionised water | | to 100.00 |
| Phase B | | |
| Ceteareth-25 | Cremaphor A25 | 1.30 |
| Glyceryl stearate and PEG-100 Stearate | Arlacel 165 | 3.25 |
| Stearic acid | | 1.30 |
| Isopropyl myristate | Estol IPM | 5.00 |
| Capric/caprylic triglyceride | Estol GTCC | 7.00 |
| Propylene glycol dicaprylate/dicaprate | Estol PDCC | 4.00 |
| Soy sterol | Generol 122 | 0.50 |
| Myristic acid | | 0.50 |
| Hydroxycetamide | Questamide H | 1.00 |
| Fragrance | Quest | 0.20 |

Hydroxycetamide is the proposed CTFA name of Questamide H (or pseudoceramide H).

The carbomer was mixed and dispersed in water, and the remaining ingredients of phase A added. The ingredients of phase B were mixed. Phase A and Phase B were both heated to 80° C. Phase B was added to phase A with shearing. Once a homogeneous mixture had been produced the mixture was stirred until cool.

This produced a homogeneous cream of pH 7.5 suitable for topical application to the skin as appropriate.

EXAMPLE 4

A cosmetic skin cream composition was made from the following ingredients:

| CFTA NAME | TRADE NAME | % W/W |
|---|---|---|
| Phase A | | |
| Carbomer | Carbopol 980 | 0.20 |
| Propylene Glycol | | 3.45 |
| Triethanolamine | | 0.20 |
| Deionised Water | | to 100.00 |
| Phase B | | |
| Ceteareth-6 Stearyl Alcohol | Cremaphor A6 | 1.00 |
| Ceteareth-25 | Cremaphor A25 | 1.00 |
| Stearic acid | | 0.80 |
| Capric/caprylic triglyceride | Miglyol 812 | 4.25 |
| Dimethicone | Silicone 200/350 | 0.80 |
| Cetyl alcohol | | 0.60 |
| Mineral oil | | 2.00 |
| Soy Sterol | Generol 122 | 0.60 |
| Hydroxycetamide | Questamide H | 6.80 |
| Phase C | | |
| Methyldibromo Glutaronitrile and Phenpoxyethanol | Euxyl K400 | 0.10 |
| Fragrance | Quest | 0.20 |

The ingredients of phase A were mixed with shearing. The ingredients of phase B were mixed. Phase A and phase B were both separately heated to 80° C. Phase B was slowly added to phase A with shearing. The mixture was cooled to 45° C. The ingredients of phase C were mixed together, and then added to the cooled mixture of phases A and B (at 45° C.), and stirred until cool.

This produced a homogeneous light, white cream of pH 6.3 suitable for topical application to the skin.

EXAMPLE 5

A cosmetic skin cream composition was made from the following ingredients:

| CFTA NAME | TRADE NAME | % W/W |
|---|---|---|
| Phase A | | |
| Carbomer | Carbopol 940 | 0.22 |
| Propylene Glycol | | 4.00 |
| Methylparaben | Nipagin M | 0.20 |
| Deionisea Water | | to 100.00 |
| Phase B | | |
| Squalene | Prisorine SQV | 6.50 |
| Mineral Oil | | 3.00 |
| Cetyl Alcohol | | 0.50 |
| Glyceryl Stearate (NSE) | Estol | 3.25 |
| Dimethicone | DC 200/350 | 0.80 |
| Lanolin Alcohol | Super Hartolan | 1.00 |
| Glyceryl Stearate (and) PEG-100 Stearate | Lexemul 561 | 3.25 |
| Propylparaben | | 0.10 |
| Proprietary Emulsifying Wax | Polawax | 3.25 |
| Isopropyl Myristate | Estol IPM | 3.10 |
| Myristic Acid | | 0.25 |
| Soy Sterol | Generol 122 | 0.35 |
| Octyl Palmitate | Estol EHP | 4.00 |
| Hydroxycetamide | Questamide H | 2.00 |
| Phase C | | |
| Triethanolamine | | 0.38 |
| Deionised Water | | 1.00 |
| Fragrance | Quest | 0.25 |
| Phase D | | |
| Imidazolidinyl Urea | Germal 115 | 0.20 |
| Deionized Water | | 3.00 |

The ingredients of phase A were mixed with shearing. The ingredients of phase B were mixed. Phase A and phase B were both separately heated to 80° C. Phase B was slowly added to phase A with shearing. The mixture was cooled to 45° C. The ingredients of phase C were then added individually to the cooled mixture of phases A and B (at 45° C). The ingredients of phase D were mixed and added to the mixture of phases A, B and C, and stirred until cool.

This produced a homogeneous rich bodied, glossy cream of pH 5.8 suitable for topical application to the skin.

EXAMPLE 6

Oil in water emulsions were made from the following ingredients:

|  |  | wt % |  |
| --- | --- | --- | --- |
| CFTA NAME | TRADE NAME | Batch 1 | Batch 2 |
| Phase A |  |  |  |
| Water |  | to 100.00 | to 100.0 |
| Methyl paraben | Nipagin M | 0.20 | 0.20 |
| Polyacrylamide (&) C13-14 Iso paraffin (&) Laureth 7 | Sepigel 305 | 1.00 | 1.00 |
| Phase B |  |  |  |
| Cetyl Alcohol |  | 3.00 | 3.00 |
| Squalene |  | 2.84 | 2.84 |
| Propyl paraben | Nipasol H | 0.15 | 0.15 |
| Pentaerythritol tetra caprate-caprylate | Crodamol PTC | 2.83 | 2.83 |
| Diisoarachidyl Dilinoleate | Liquiwax DIEFA | 2.83 | 2.83 |
| Cetearth-20 | Empilan KM20 | 3.00 | 3.00 |
| Dimethicone | Silicone 200/350 | 0.50 | 0.50 |
| Hydroxycetamide | Questamide B | — | 2.00 |
| Phase C |  |  |  |
| Water |  | 2.00 | 2.00 |
| Imidazolidinyl Urea | Germal 115 | 0.15 | 0.15 |
|  | pH | 6.80 | 6.80 |

The emulsions were made by stirring the Sepigel 305 into cold water of phase A until it was dispersed. The remaining ingredients of phase A were then added. The ingredients of phase B were mixed. Phase A and phase B were both heated to 80° C. Phase B was added to phase A whilst shearing. Once a homogenous mixture had been produced the mixture was stirred until cool. The ingredients of phase C were mixed together, added to the cooled mixture of phases A and B and further mixed.

The viscosity of batches 1 and 2 was tested on a Viscometers UK machine, model ERV-8, using the heliopathe, and results were as follows:

|  | Batch 1 | Batch 2 |
| --- | --- | --- |
| T-Bar | B | B |
| Speed | 10 | 10 |
| CPS | 2080 | 18160 |

These show that batch 2, which includes 2.00% pseudoceramide H, has a much higher viscosity than batch 1, which does not include pseudoceramide H.

EXAMPLE 7

Oil in water emulsions were made from the following ingredients:

| CFTA NAME | TRADE NAME | Batch 1 | Batch 2 |
| --- | --- | --- | --- |
| Phase A |  |  |  |
| Water |  | to 100.00 | to 100.00 |
| Methyl paraben | Nipagin M | 0.20 | 0.20 |
| Phase B |  |  |  |
| Avocado Oil |  | 2.00 | 2.00 |
| Isopropyl myristate |  | 7.00 | 7.00 |
| Cetyl alcohol |  | 0.50 | 0.50 |
| Ceteareth-20 | Empilan KM20 | 1.00 | 1.00 |
| Dimethicone | Silicone 200/350 | 1.00 | 1.00 |
| Propyl paraben | Nipasol M | 0.10 | 0.10 |
| Hydroxycetamide | Questamide H | — | 2.00 |
| Phase C |  |  |  |
| Water |  | 2.00 | 2.00 |
| Imidazolidinyl Urea | Germal 115 | 0.15 | 0.15 |
|  | pH | 7.40 | 7.10 |

The emulsions were made by separately mixing the ingredients of phases A and B and heating the 2 mixtures to 70° C. Phase B was added to phase A whilst shearing. Once a homogenous mixture had been produced the mixture was stirred until cool.

The viscosity of batches 1 and 2 was tested on a Viscometers UK machine, model ERV-8, and results were as follows:

|  | Batch 1 | Batch 2 |
| --- | --- | --- |
| Spindle | R3 | R3 |
| Speed | 10 | 10 |
| CPS | 30 | 7230 |

These show that batch 2, which includes 2.00% pseudoceramide H, has a much higher viscosity than batch 1, which does not include pseudoceramide H.

We claim:

1. A compound of the general formula:

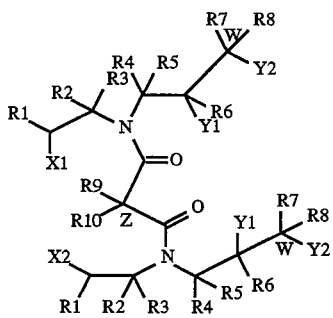

in which:

R1 is an aliphatic hydrocarbon of 10 of 24 atoms; R2–R8 are each independently H or $CH_3$;

R9 and R10 are each independently H or a hydrocarbon group of up to 24 C atoms;

X1 and X2 are independently H or OH;

Y1 and Y2 are independently H or OH, while at least one of Y1 and Y2 is OH: and

Z is a carbon atom and W is a carbon atom which is only optionally present.

2. A compound according to claim 1 wherein R1 has 16 to 18 C atoms.

3. A compound according to claim 1 wherein the groups —C(R4R5)—C(Y1R6)—C(R7R8Y2) are $CH_2$—$CH_2$—OH, $CH_2$—CHOH—$CH_2$OH, $CH_2$—$CH_2$—$CH_2$OH or $CH_2$—CHOH—$CH_3$.

4. A compound according to claim 1 wherein R9 and R10 are both hydrogen.

5. A compound according to any one of claim 1, wherein one of R9 and R10 is an aliphatic hydrocarbon group of up to 24 C atoms and the other is H.

6. A compound having the formula:

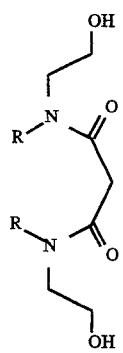

in which R is an aliphatic hydrocarbon having 10–18 C atoms.

7. A compound according to claim 3 wherein R2 and R3 are both hydrogen and X1 and X2 are both OH.

8. A composition suitable for topical application to skin, hair or nails, comprising one or more compounds according to any one of claim 1 and a carrier vehicle.

9. A composition according to claim 8 wherein the compounds according to the claim 1 are present in an amount of between 0.0001 to 50% by weight.

10. A method of treating skin, hair or nails comprising topical application of a composition according to claim 8 or claim 9.

11. A compound according to claim 6 wherein R is $C18H_{37}$, $C_{14}H_{29}$, $C_{16}H_{33}$, $C_{12}H_{25}$ or $C_{10}H_{21}$.

12. A compound according to claim 1 which is pseudoceramide E or H.

* * * * *